(12) United States Patent
Ishitsu et al.

(10) Patent No.: US 10,299,746 B2
(45) Date of Patent: May 28, 2019

(54) RADIATION IMAGING APPARATUS

(71) Applicant: HITACHI, LTD., Tokyo (JP)

(72) Inventors: Takafumi Ishitsu, Tokyo (JP); Isao Takahashi, Tokyo (JP); Kazuma Yokoi, Tokyo (JP); Makoto Satou, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 16/063,706

(22) PCT Filed: Dec. 21, 2016

(86) PCT No.: PCT/JP2016/088226
§ 371 (c)(1),
(2) Date: Jun. 19, 2018

(87) PCT Pub. No.: WO2017/122514
PCT Pub. Date: Jul. 20, 2017

(65) Prior Publication Data
US 2018/0368790 A1 Dec. 27, 2018

(30) Foreign Application Priority Data
Jan. 12, 2016 (JP) ................. 2016-003304

(51) Int. Cl.
*A61B 6/00* (2006.01)
*A61B 6/03* (2006.01)
(Continued)

(52) U.S. Cl.
CPC .............. *A61B 6/4291* (2013.01); *A61B 6/00* (2013.01); *A61B 6/03* (2013.01); *A61B 6/032* (2013.01);
(Continued)

(58) Field of Classification Search
CPC ..... A61B 6/032; A61B 6/4266; A61B 6/4291; G01T 1/241
See application file for complete search history.

(56) References Cited

U.S. PATENT DOCUMENTS

2004/0013224 A1  1/2004  Baba et al.
2009/0080601 A1  3/2009  Tkaczyk et al.
(Continued)

FOREIGN PATENT DOCUMENTS

JP  2002-022678 A  1/2002
JP  2009-078143 A  4/2009
(Continued)

OTHER PUBLICATIONS

International Search Report of PCT/JP2016/088226 dated Mar. 28, 2017.

*Primary Examiner* — Marcus H Taningco
(74) *Attorney, Agent, or Firm* — Mattingly & Malur, PC

(57) ABSTRACT

A radiation imaging apparatus provided with a detector capable of improving correction accuracy at a high counting rate. The present invention is provided with: grids that remove scattered beams that emanate from an object; and a plurality of detector sub-pixels arranged so as to divide the gap between the grids into three or more segments, wherein the area of each of the detector sub-pixels located below the wall surface of the grids is larger than that of each of the other detector sub-pixels in a planar view. The size of each of the detector sub-pixels not located below the wall surface of the grids is expressed as $(P_g - T_g - L_{split} \times 2)/N$, where $P_g$ represents the pitch between the grids, $T_g$ represents the thickness of each of the grids, and N represents the number of segments formed by the detector sub-pixels between the grids.

6 Claims, 8 Drawing Sheets

(51) Int. Cl.
*G01T 1/24* (2006.01)
*G01T 7/00* (2006.01)

(52) U.S. Cl.
CPC .............. *A61B 6/4266* (2013.01); *G01T 1/24* (2013.01); *G01T 1/241* (2013.01); *G01T 7/00* (2013.01)

(56) References Cited

U.S. PATENT DOCUMENTS

2014/0321610 A1  10/2014  Ueki et al.
2015/0030128 A1  1/2015   Oikawa

FOREIGN PATENT DOCUMENTS

WO  2013/089154 A1  6/2013
WO  2013/140445 A1  9/2013

[Fig. 1]
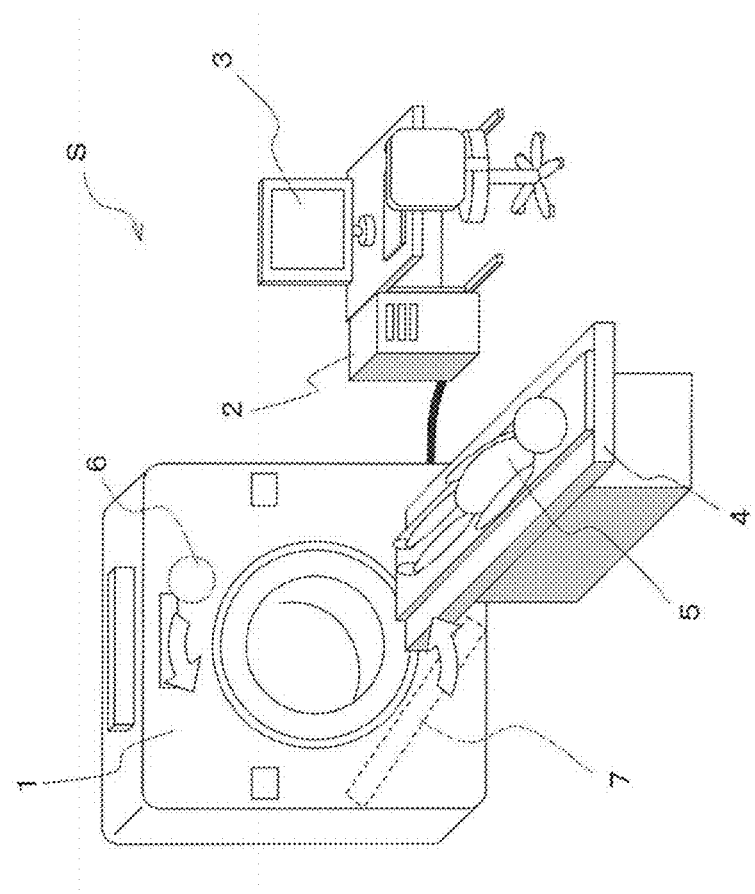

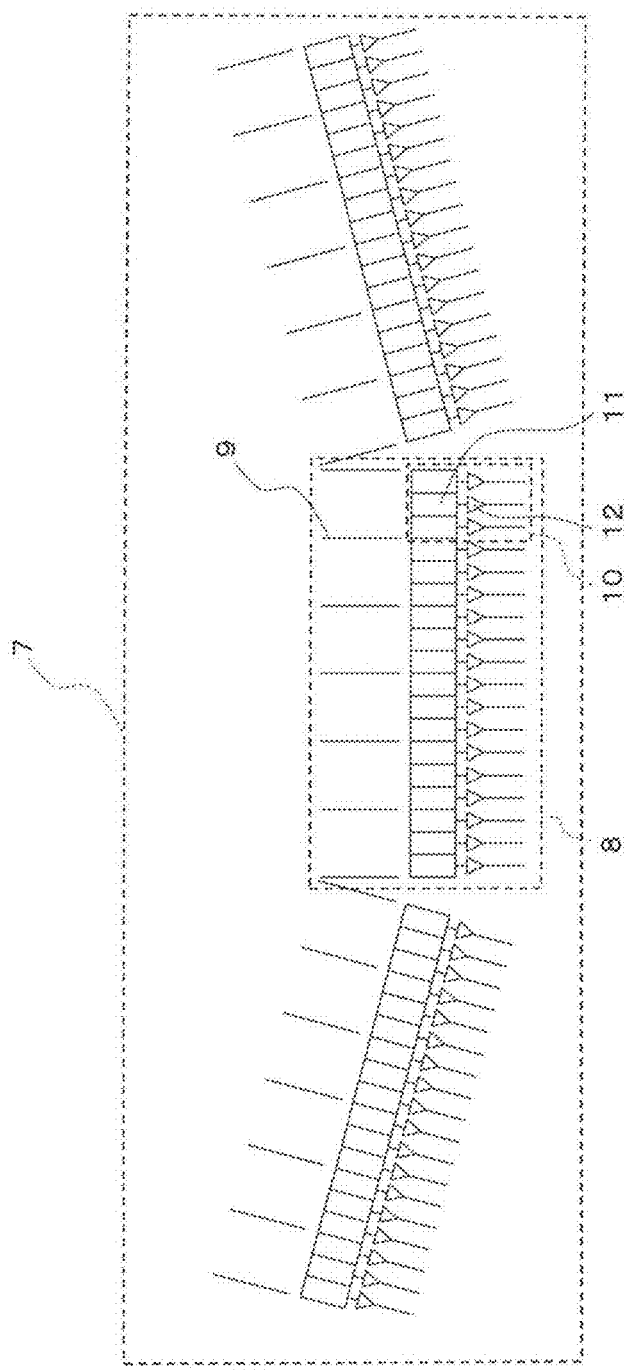
[Fig. 2]

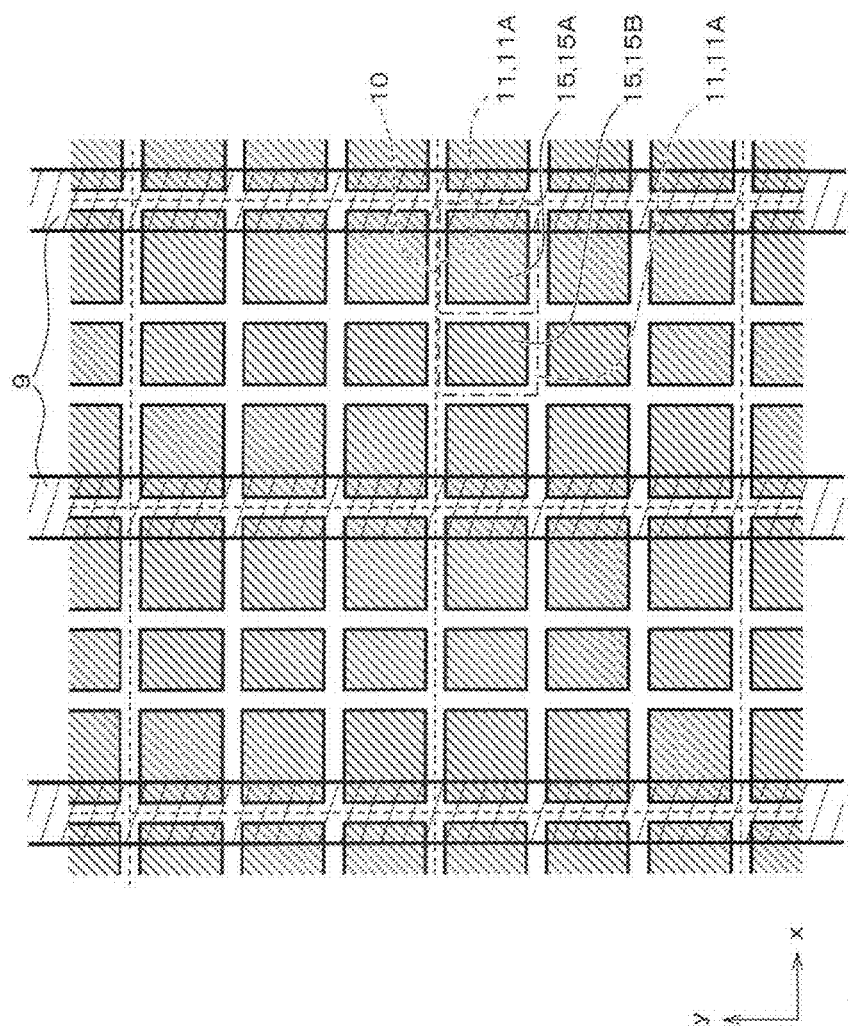
[Fig. 3]

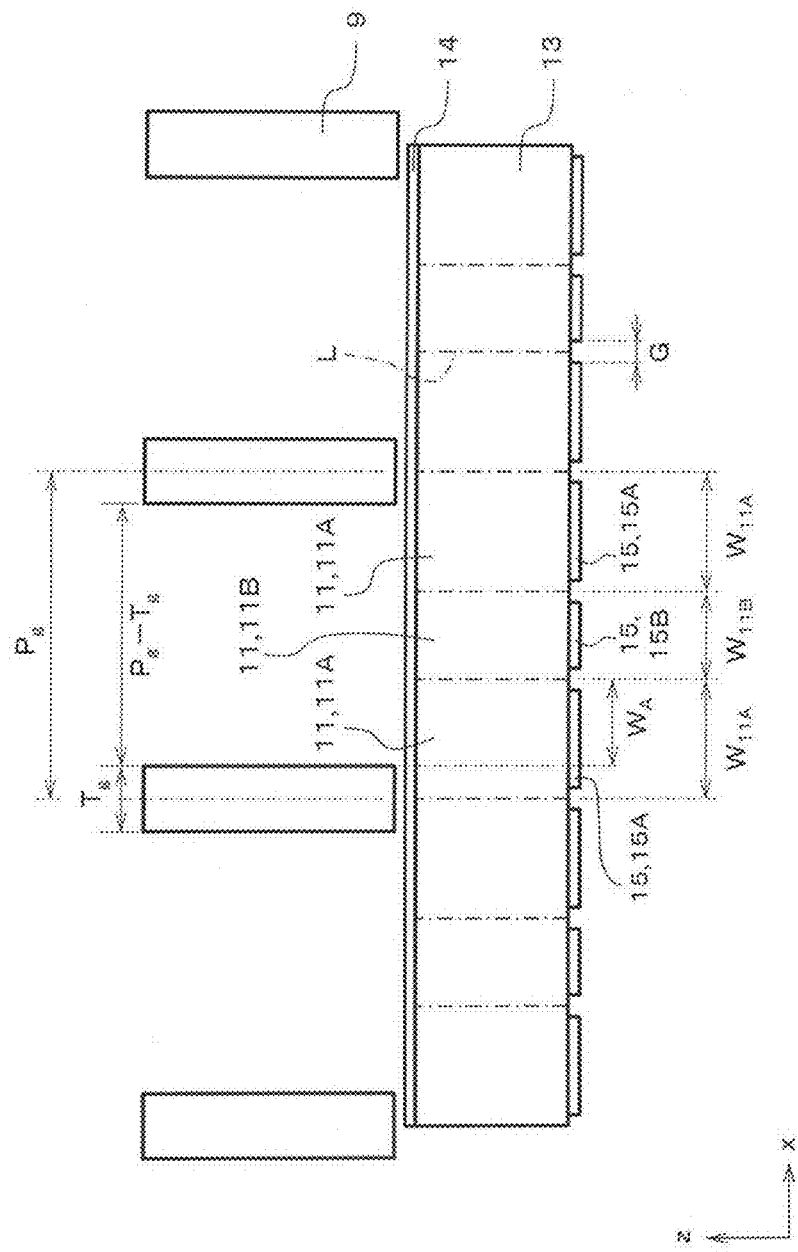
[Fig. 4]

[Fig. 5]
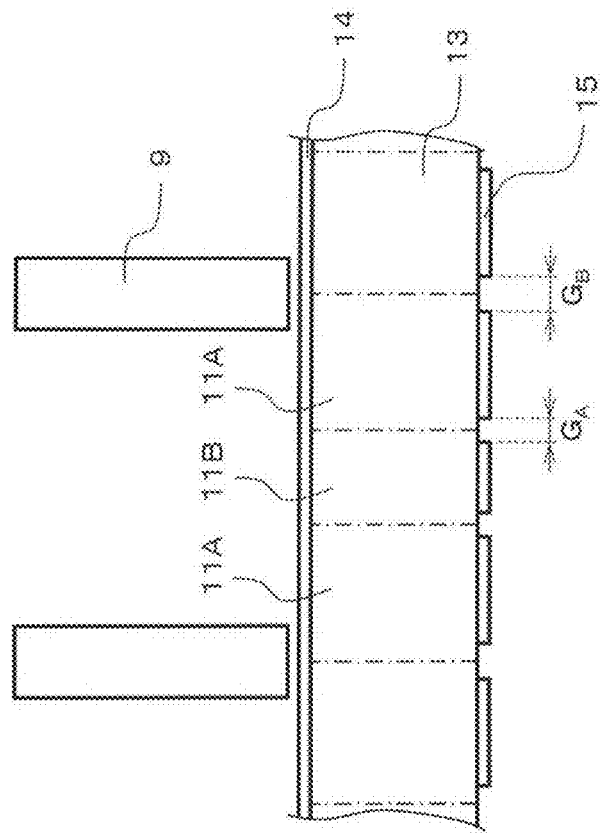

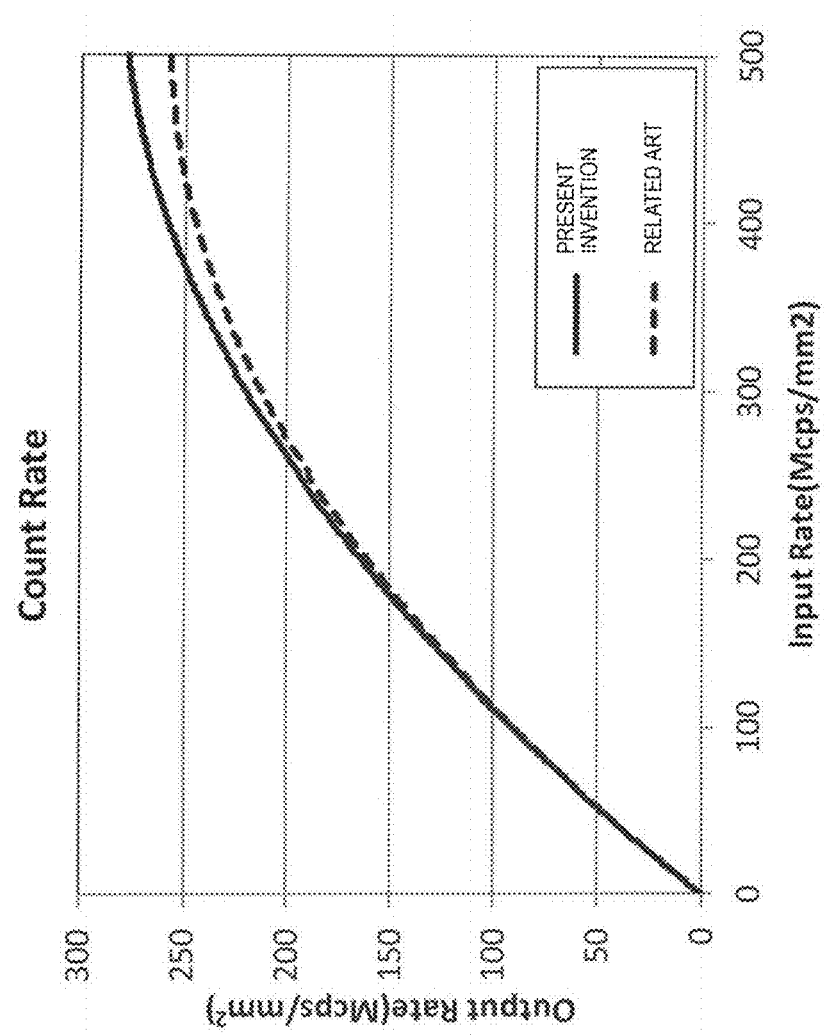
[Fig. 6]

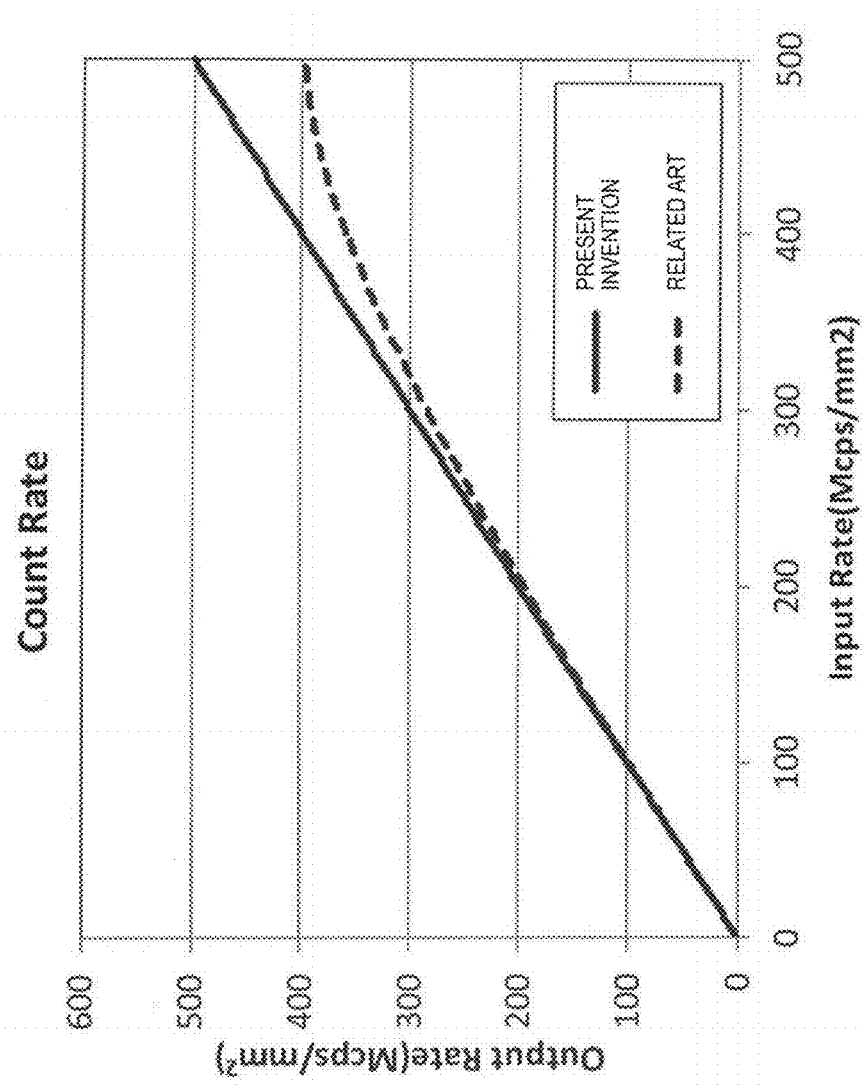
[Fig. 7]

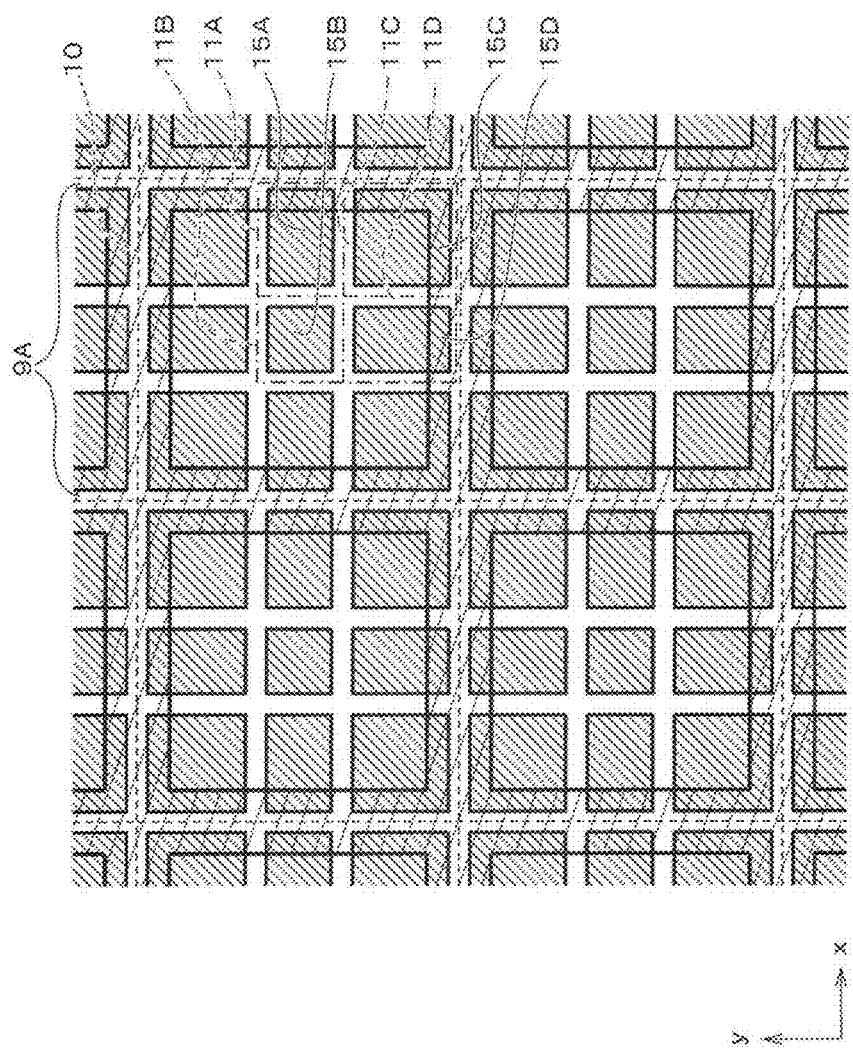
[Fig. 8]

RADIATION IMAGING APPARATUS

BACKGROUND OF THE INVENTION

Field of the invention

The present invention relates to a radiation imaging apparatus, and more particularly to a structure of a detector in the radiation imaging apparatus using a semiconductor as a detector.

Description of Related Art

An X-ray computed tomography (CT) serving as one of radiation imaging apparatus is an apparatus that obtains a tomographic image of a subject from attenuation when X-rays generated from an X-ray tube transmit the subject. In an X-ray detector provided in this X-ray CT apparatus, a technique is known to design so as to have a large pixel size and a reduced number of electric charge sharing boundaries at low flux, and so as to have a small non-saturated pixel size in the portion when a portion of a CT detector is receiving a high flux (PTL 1). That is, the X-ray detector includes a plurality of metallized anodes that collects electric charge generated in a direct conversion material, a readout device, and a plurality of switches, and includes a redistribution layer having a plurality of electrical paths that deliver the electric charge from the plurality of metallized anodes to at least one readout device. Furthermore, each of the plurality of switches includes an input line coupled to one of the plurality of metallized anodes, a first output node coupled to at least one readout device, and a second output node coupled to the other switch.

CITATION LIST

Patent Literature
PTL 1: JP-A-2009-78143

SUMMARY OF INVENTION

Technical Problem

Incidentally, in an actual radiation detector, a grid is disposed to remove scattered beams on a radiation incident side. Therefore, when a small unsaturated pixel (detector sub-pixel) size is set as a size of detector pixel equally divided, in a case where the number of the segments is increased, there is a situation in which sensitivity is different for each detector sub-pixel due to interference between the detector sub-pixel and the grid, so that correction accuracy is reduced.

Therefore, it is an object of the present invention to provide a radiation imaging apparatus provided with a detector capable of improving correction accuracy under a high counting rate.

Solution to Problem

In order to solve such a problem, a radiation imaging apparatus according to the present invention includes a grid that removes scattered beams that emanate from an object, and a plurality of detector sub-pixels arranged so as to divide a gap between the grids into three or more segments, in which an area of each of detector sub-pixels located below wall surfaces of the grids is larger than that of each of the other detector sub-pixels in plan view.

In addition, a radiation imaging apparatus according to the present invention includes a grid that removes scattered beams that emanate from an object, a semiconductor element, a common electrode formed on one surface of the semiconductor element, and a divided electrode formed on the other surface of the semiconductor element, in which an area of each of the divided electrodes located below wall surfaces of the grids is larger than that of each of the other divided electrodes in plan view.

Advantageous Effects of Invention

According to the present invention, it is possible to provide the radiation imaging apparatus provided with the detector capable of improving the correction accuracy under the high counting rate.

BRIEF DESCRIPTION OF DRAWINGS

FIG. 1 is a configuration diagram of a radiation imaging apparatus according to a first embodiment.

FIG. 2 is a configuration diagram of a detector panel provided in the radiation imaging apparatus according to the first embodiment.

FIG. 3 is a diagram illustrating a positional relationship between a detector pixel, a detector sub-pixel, and a grid as viewed from an incident direction of X-rays relating to the detector panel of the radiation imaging apparatus according to the first embodiment.

FIG. 4 is a diagram illustrating a positional relationship between a detector pixel, a detector sub-pixel, and a grid as viewed from a body axis direction relating to the detector panel of the radiation imaging apparatus according to the first embodiment.

FIG. 5 is a diagram illustrating other positional relationship between the detector pixel, the detector sub-pixel, and the grid as viewed from the body axis direction relating to the detector panel of the radiation imaging apparatus according to the first embodiment.

FIG. 6 is a graph illustrating a difference in a counting rate between the radiation imaging apparatus according to the first embodiment and a radiation imaging apparatus in the related art.

FIG. 7 is a graph illustrating a counting rate after correction for the difference in the counting rate between the radiation imaging apparatus according to the first embodiment and the radiation imaging apparatus in the related art.

FIG. 8 is a diagram illustrating a positional relationship between a detector pixel, a detector sub-pixel, and a grid as viewed from an incident direction of X-rays relating to a detector panel of a radiation imaging apparatus according to a second embodiment.

PREFERRED EMBODIMENT OF THE INVENTION

In X-ray imaging, the number of radiation generation is large and a counting rate of a detector is high, so that it is necessary to reduce the counting rate per circuit by dividing detector pixels in a photon counting CT. Therefore, detectors are disposed at a pitch of approximately 1 mm in the detectors of the X-ray CT in the related art, whereas in the photon counting CT, detector sub-pixels obtained by dividing the detector pixels into, for example, 0.5 mm to 0.05 mm pitch are used. However, even when the detector pixels are divided, a very high counting rate of several tens of Mcps per detector sub-pixel is required, and the dead time of the circuit has a significant influence. In addition, in CT, the required accuracy for the linearity of the count number is very high, and it is necessary to enhance the correction accuracy when the dead time occurs.

Since a complex calculation is required to correct the dead time, although correction processing is performed after transferring the data to a workstation for image reconstruction, since the data transfer amount is enormous when data of the detector sub-pixel miniaturized at the time of data transfer is transferred as it is, it is desirable to total the count number of the detector sub-pixel and transfer the total count number as the count number of the detector pixels. In this case, when the sensitivity of each detector sub-pixel is not uniform, the calculation for correction is complicated, and there is a problem that the correction accuracy decreases. In addition, when there is a variation in the counting rate between sub-pixels, there is also a problem that the performance of the device is determined by saturation of the sub-pixels having the highest counting rate, and it is desirable that the sensitivity of the detector sub-pixels is uniform.

In this manner, in order to improve the correction accuracy of the dead time under the high counting rate, it is desirable that the sensitivity of each detector sub-pixel is uniform. Since the sensitivity of the detector is substantially determined by the area thereof, the sensitivity of the detector pixels can be made uniform by equally dividing the detector pixels when making the detector sub-pixels. However, in reality, since a grid for removing scattered beams is disposed on the radiation incident side of the detector, when the number of the segments formed by the detector pixels is increased by equal division, due to the interference between the detector sub-pixel and the grid, there is a situation in which the sensitivities are different for each detector sub-pixel, and there is a possibility that the correction accuracy is decreased.

Hereinafter, aspects (hereinafter referred to as "embodiment") for performing the present invention will be described in detail with reference to the drawings as appropriate. In each drawing, common parts are denoted by the same reference numerals, and redundant description is omitted.

FIRST EMBODIMENT

<Radiation Imaging Apparatus>

A radiation imaging apparatus S according to a first embodiment will be described with reference to FIG. 1. FIG. 1 is a configuration diagram of the radiation imaging apparatus S according to the first embodiment.

As illustrated in FIG. 1, an X-ray CT apparatus (radiation imaging apparatus) S is provided with a gantry 1, a data processing device 2 that processes the collected data to reconstruct an image, an image display device 3 that displays the processed image, and a bed 4 that hold a subject 5.

The bed 4 can horizontally move toward the opening of the gantry 1, and moves the subject 5 to the imaging position (not illustrated) in the gantry 1.

In the gantry 1, an X-ray tube 6 and a detector panel 7 are disposed to face each other. The X-ray tube 6 and the detector panel 7 rotate approximately once to three times per second in a state where a periphery of the subject 5 moved in the gantry 1 is opposed, and acquire projection images from each direction of the subject 5.

The X-ray tube 6 accelerates electrons by applying a high voltage of approximately 100 kV and generates X-rays by applying the electrons to a target. The generated X-rays transmit the subject 5 and reach the detector panel 7. At this time, since the intensity of X-rays is attenuated by the subject 5, information in the body of the subject 5 can be acquired by knowing the amount of attenuation. In addition, means such as changing the voltage of the X-ray tube 6 in order to know the difference in the amount of attenuation due to energy is used.

The data acquired by the detector panel 7 is transferred to the data processing device 2, where correction and image reconstruction processing are performed. Thereafter, a tomographic image reconstructed by the data processing device 2 is displayed on the image display device 3.

<Detector Panel 7>

Next, the detector panel 7 provided in the radiation imaging apparatus S according to the first embodiment will be further described with reference to FIG. 2. FIG. 2 is a configuration diagram of the detector panel 7 provided in the radiation imaging apparatus S according to the first embodiment. FIG. 2 is the diagram of the detector panel 7 as seen in a body axis direction (slice direction, direction of rotation center axis of X-ray tube 6 and detector panel 7 in FIG. 1, and y direction in FIG. 3).

As illustrated in FIG. 2, the detector panel 7 is configured to include a plurality of detector modules 8, and the plurality of detector modules 8 are arranged on an arc centered on a position of the X-ray tube 6 (refer to FIG. 1).

The detector module 8 is configured to include a grid 9 and a plurality of detector pixels 10. Furthermore, the detector pixel 10 is formed of a plurality of detector sub-pixels 11, and a readout circuit 12 for reading a signal is connected to each detector sub-pixel 11.

When the X-rays transmit the subject 5 (refer to FIG. 1), a portion of the X-rays are scattered, and the traveling direction thereof changes. Since such X-rays cause image blurring, it is desirable to remove such X-rays, and therefore the grid 9 is provided. The grid 9 is made of a material such as tungsten which has high stopping power of X-rays. In addition, in order to increase the transmission efficiency of the incident X-rays, a thin plate as much as possible is used. For the plate of the grid 9, in order to reduce the influence of deflection and the error of the X-ray generation position, a plate of which thickness gradually changes with respect to an incident direction of X-rays may be used, or T-shaped plate with increased thickness only at a portion close to the detector, instead of a flat plate.

Here, the structure of the detector sub-pixel 11 will be described with reference to FIG. 4. FIG. 4 is a diagram of the detector panel 7 of the radiation imaging apparatus S according to the first embodiment as viewed from the body axis direction. The detector sub-pixel 11 is made of CdTe or CdZnTe, and a plurality of detector sub-pixels 11 are formed in a semiconductor element 13 including one semiconductor crystal. Electrodes are formed on two opposing surfaces of the semiconductor crystal, respectively. On one surface (side on which X-rays are incident, and side on which grid 9 is located), a common electrode 14 is formed on the entire surface, and a high voltage for charge collection is applied. On the other surface (side opposite to side on which X-rays are incident), a pixelated individual electrode 15 is formed so as to read a charge signal. The electrode on the other surface is divided as the individual electrode 15, so that the plurality of detector sub-pixels 11 is formed. That is, one individual electrode 15 corresponds to one detector sub-pixel 11. The electrode is formed by patterning using gold or platinum. The length of a side of the detector is approximately 10 mm to 20 mm, when the pixel is 0.5 mm, 20 to 40 pixels are arranged in a row, and since the pixels are arranged in a plane, hundreds to thousands of pixels are formed in one semiconductor element 13. The thickness of the semiconductor element 13 is sufficient to detect X-rays, and the thickness of the semiconductor element 13 is approximately 2 mm in a medical X-ray CT apparatus.

In FIG. 2, when X-rays are incident on each detector sub-pixel 11, a charge signal is generated, which signal is read out by the readout circuit 12. Although information on energy is obtained for each X-ray photon from the readout circuit 12, information on energy is classified for each predetermined threshold value, and the number of X-rays entering a specific energy range is counted. In the photon counting CT, since the number of detector sub-pixels 11 is significantly large, information on the plurality of detector sub-pixels 11 included in the detector pixel 10 is totaled and transferred to the data processing device 2.

In the radiation imaging apparatus S according to the first embodiment, although the transfer of data from the detector panel 7 (readout circuit 12) to the data processing device 2 is described as transfer in which the count number of the detector sub-pixel 11 is totaled and transferred as the count number of the detector pixel 10, the present invention is not limited thereto. Regardless of the physical pixels, for example, a method of compressing data by totaling the count numbers of two detector sub-pixels 11 and transferring in a certain axial direction may be used. In addition, the count number of the detector sub-pixel 11 may be configured to be transferred as it is without being totaled. By reconstructing the image using information on the sub-pixels as they are, it is possible to acquire a more accurate image.

<Positional Relationship between Detector Pixel 10, Detector Sub-pixel 11, and Grid 9>

Next, a positional relationship between the detector pixel 10, the detector sub-pixel 11, and the grid 9 will be further described with reference to FIGS. 3 and 4. FIG. 3 is a diagram illustrating the positional relationship between the detector pixel 10, the detector sub-pixel 11, and the grid 9 as viewed from an incident direction of X-rays (in plan view) relating to the detector panel 7 of the radiation imaging apparatus S according to the first embodiment.

In a case of viewing the detector panel 7 from the incident direction of X-rays, although the individual electrodes 15 serving as pixelated electrodes cannot be seen (refer to FIG. 4), the positions of the individual electrodes 15 are illustrated with hatching to the left downward in FIG. 3. In addition, the grid 9 is illustrated with hatching to the right downward in FIG. 3. In addition, a boundary of the detector pixel 10 is illustrated by broken lines, and a boundary of a portion of the detector sub-pixels 11 (11A, 11B) is illustrated by one-dot chain lines in FIG. 3.

As illustrated in FIG. 3, the grid 9 of the radiation imaging apparatus S according to the first embodiment is referred to as a one-dimensional (1D) grid. The grid 9 is installed along the body axis direction (y direction) and has a wall that removes the scattered beams in one direction (x direction).

The detector pixels 10 are present so as to be interposed between the grids 9, and the detector pixels 10 are regularly arranged to constitute the detector panel 7 (refer to FIG. 2). In the example of FIG. 3, the detector pixel 10 is formed of 3×3 detector sub-pixels 11. The number of the detector sub-pixels 11 constituting the detector pixel 10 is not limited to this number and may be 4×4, 4×3, or the like.

The detector sub-pixel 11 is formed by attaching a patterned individual electrode 15 to the surface of the semiconductor element 13 (refer to FIG. 4). Since the electric charge generated between the individual electrode 15 and the adjacent individual electrode 15 (between electrodes) is also attracted to either of the individual electrodes 15, the center between the electrodes is the boundary of the detector sub-pixel 11.

As illustrated in FIG. 3, the size of the detector sub-pixel 11 is different depending on the relative position with respect to the grid 9. Here, in a case where three or more detector sub-pixels 11 are arranged with respect to the grid 9 (three in case of FIG. 3), the detector sub-pixel 11 is divided into two of the detector sub-pixel 11A partially located below the grid 9 and the detector sub-pixel 11B not located below the grid 9 as viewed from the incident direction of the X-ray. In other words, the detector sub-pixel 11A has a portion located below the wall surface of the grid 9, and the detector sub-pixel 11B does not have a portion located below the wall surface of the grid 9 as seen from the incident direction of the X-ray. The radiation in the X-ray CT apparatus S is substantially uniformly incident on the detector module 8, but is blocked by the grid 9, so that the X-rays reaching the detector pixel 10 are not uniform. Therefore, in the detector panel 7 of the radiation imaging apparatus S according to the first embodiment, the area of the detector sub-pixel 11B not located below the grid 9 is made smaller than that of the detector sub-pixel 11A located below the grid 9 when viewed from the incident direction of the X-ray (in plan view), so that the sensitivity is brought close to uniformity.

FIG. 4 is a diagram illustrating the positional relationship between the detector pixel 10, the detector sub-pixel 11, and the grid 9 as viewed from the body axis direction relating to the detector panel 7 of the radiation imaging apparatus S according to the first embodiment.

Here, the boundary L of the detector sub-pixel 11 is the center between the individual electrode 15 and the adjacent individual electrode 15 (between electrodes), and the detector sub-pixel 11 is determined by the arrangement of the individual electrodes 15. Therefore, the width ($W_{11A}$, $W_{11B}$) of the detector sub-pixel 11 is a pitch between the centers of the electrodes of the individual electrode 15 (gap center).

In a case where $P_g$ represents the pitch of the grid 9, $T_g$ represents the thickness of each of the grids 9, and N represents the number of the segments of the detector sub-pixel 11 with respect to the grid between the grids 9, the width $W_{11B}$ of the detector sub-pixel 11B not located below the grid 9 is set to as

[Math. 1]

$$W_{11B} = \frac{(P_g - T_g)}{N}, \tag{1}$$

and the width $W_{11A}$ of the detector sub-pixel 11A located below the grid 9 is set to as

[Math. 2]

$$W_{11A} = W_A + \frac{T_g}{2} = \frac{(P_g - T_g)}{N} + \frac{T_g}{2}, \tag{2}$$

so that the width $W_A$ not blocked by the grid 9 of the detector sub-pixel 11A and the width $W_{11B}$ of the detector sub-pixel 11B when viewed from the incident direction of the X-ray can be made equal. That is, the area of the detector sub-pixel 11A not blocked by the grid 9 and the area of the detector sub-pixel 11B when viewed from the incident direction of the X-ray can be made equal to each other, and it is possible to bring the sensitivity of the detector sub-pixel 11 substantially uniform. In addition, the sensitivity of the detector sub-pixel 11 is made close to uniformity, so that the radiation imaging apparatus S can improve the correction accuracy of the dead time under a high counting rate.

In a case where the grid 9 is configured to include rather than a parallel plate, the thickness $T_g$ of the grid 9 can be calculated by the thickness of the grid wall covering the detector pixel 10.

In addition, when the distance (gap) between the electrodes is G, the width of the divided electrode 15B of the detector sub-pixel 11B not located below the grid 9 is set to as

[Math. 3]

$$\frac{(P_g - T_g)}{N} - G, \qquad (3)$$

and the width of the divided electrode 15A of the detector sub-pixel 11A located below the grid 9 is set to as

[Math. 4]

$$\frac{(P_g - T_g)}{N} + \frac{T_g}{2} - G, \qquad (4)$$

so that it is possible to bring the sensitivity of the detector sub-pixel 11 substantially uniform.

In order to bring the sensitivity of the detector sub-pixel 11 closer to uniformity, it is necessary to consider the reaction in the detector. Since the detector sub-pixel 11 is formed of one semiconductor element 13, a phenomenon occurs in which X-rays reacted in the vicinity of the boundary L of the detector sub-pixel 11 are detected over two adjacent detector sub-pixels 11. Therefore, it is impossible to completely equalize the sensitivity of the detector sub-pixel 11 only by equally dividing the opening of the grid (that is, $W_A = W_{11B}$). The reason why X-rays are detected by two adjacent detector sub-pixels 11 depends on the energy of the X-rays and the configuration of the detector, but the width is approximately 0 to 60 μm around the boundary L (each width of approximately 0 to 30 μm from boundary L).

Since no X-rays are incident under the grid 9, the effect occurs only at one end portion in the detector sub-pixel 11A located below the grid 9. On the other hand, in the detector sub-pixel 11B not located below the grid 9, the effect occurs at the two end portions. In a case where the range where the effect occurs is set to the range of one side $L_{split}$ from the boundary L, the width of the detector sub-pixel 11 is set so as to be

[Math. 5]

$$W_A + L_{split} = W_{11B} + L_{split} \times 2$$

In other words, the width $W_{11B}$ [μm] of the detector sub-pixel 11B not located below the grid 9 is set to as

[Math. 6]

$$W_{11B} = \frac{(P_g - T_g)}{N} - \frac{L_{split} \times 2}{N}, \qquad (6)$$

and the width $W_{11A}$ [μm] of the detector sub-pixel 11A located below the grid 9 is set to as

[Math. 7]

$$W_{11A} = \frac{(P_g - T_g)}{N} - \frac{L_{split} \times 2}{N} + L_{split} + \frac{T_g}{2}, \qquad (7)$$

so that the sensitivity of the detector sub-pixel 11 can be brought closer to uniformity.

That is, the width $W_{11B}$ of the detector sub-pixel 11B not located below the grid 9 is set to as

[Math. 8]

$$\frac{(P_g - T_g - L_{split} \times 2)}{N}$$

(herein, $L_{split}$ is in the range of 0 μm to 30 μm depending on detector system and energy). Therefore, the sensitivity of the detector sub-pixel 11 can be brought closer to uniformity in consideration of a phenomenon that X-rays incident near the boundary L are detected across the two detector sub-pixels 11. As a result, the radiation imaging apparatus S can further improve the correction accuracy of the dead time under the high counting rate.

In addition, when the distance (gap) between the electrodes is G, the width of the divided electrode 15B of the detector sub-pixel 11B not located below the grid 9 is set to as

[Math. 9]

$$\frac{(P_g - T_g - L_{split} \times 2)}{N} - G.$$

Therefore, it is possible to bring the sensitivity of the detector sub-pixel 11 closer to uniformity.

FIG. 5 is a diagram of the detector panel 7 of the radiation imaging apparatus S according to the modification example of the first embodiment as viewed from the body axis direction. In a case where the potentials of the individual electrodes 15 are all the same as each other, the boundary of the detector sub-pixel 11 coincides with the line passing through the center between the electrodes. Therefore, in the radiation imaging apparatus S according to the first embodiment illustrated in FIGS. 3 and 4, in order to make the width $W_{11B}$ of the detector sub-pixel 11B on the lower side of the grid 9 larger than the width $W_{11A}$ of the detector sub-pixel 11A, the width of the electrode 15B is made larger than the width of the individual electrode 15A. On the other hand, in the radiation imaging apparatus S according to the modification example illustrated in FIG. 5, in addition to making the width of the individual electrode 15B larger than the width of the individual electrode 15A, the gap $G_B$ between the individual electrodes 15 on the lower side of the grid 9 is made wider than the gap $G_A$ between the individual electrodes 15 not on the lower side of the grid 9, so that the width $W_{11B}$ of the detector sub-pixel 11B on the lower side of the grid 9 is made larger than the width $W_{11A}$ of the detector sub-pixel 11A. Even with such a configuration, it is possible to obtain the same operational effect as that in the first embodiment. However, in the case of the configuration illustrated in FIG. 5, it is desirable to take measures against charge-up on the electrode surface.

<Effect>

The effect of the radiation imaging apparatus S according to the first embodiment will be further described with reference to FIGS. 6 and 7. FIG. 6 is a graph illustrating a difference in counting rate between the radiation imaging apparatus S according to the first embodiment (present invention) and the radiation imaging apparatus in the related art. This graph illustrates the output rate of the circuit with respect to the incident rate of X-rays, and the closer to the straight line is the higher performance apparatus. The output rate is a value after addition of a plurality of pixels. In the detector of the radiation imaging apparatus in the related art, since the sensitivity varies for each pixel, counting rate characteristics deteriorate because the count of the output rapidly decreases in pixels with high sensitivity as the X-ray incidence rate increases. On the other hand, in the detector of the radiation imaging apparatus S according to the first embodiment (present invention), since the sensitivity becomes uniform, the amount of decrease becomes gentle. This effect appears more remarkably when correction is performed.

FIG. 7 is a graph illustrating a counting rate after correction for the difference in the counting rate between the radiation imaging apparatus S according to the first embodiment and the radiation imaging apparatus in the related art. When correction is performed by estimating from the dead time of the circuit, the counting rate becomes almost linear in the present invention, but in the method in the related art, it is difficult to correct and the counting rate deviates from the straight line. As a matter of course, although the counting rate improves by adjusting the value used for correction even in the method in the related art, the maximum counting rate is deteriorated, and it is required to estimate the value for correction based on actual measurement, not based on the design value of the circuit.

SECOND EMBODIMENT

Next, the radiation imaging apparatus S according to a second embodiment will be described. FIG. 8 is a diagram illustrating a positional relationship between a detector pixel 10, a detector sub-pixel 11, and a grid 9A as viewed from an incident direction of X-rays relating to a detector panel 7 of a radiation imaging apparatus S according to the second embodiment.

In FIG. 8 similar to FIG. 3, the positions of the individual electrodes 15 are illustrated with hatching to the left downward, the grid 9A is illustrated with hatching to the right downward, a boundary of the detector pixel 10 is illustrated by broken lines, and a boundary of a portion of the detector sub-pixels 11 (11A to 11D) is illustrated by a one-dot chain lines.

The radiation imaging apparatus S according to the second embodiment is different from the radiation imaging apparatus S (refer to FIG. 3) according to the first embodiment in that the grid 9A is referred to as a two-dimensional (2D) grid in which the grid 9A is not only in one direction but also in a lattice shape. The grids 9A are installed along the body axis direction (y direction) and the circumferential direction (x direction), walls of the grid 9A have a lattice shape, and the openings thereof are square.

In FIG. 8, the pitch and the thickness of the grid 9A are the same as these in the x and y directions, but in the radiation imaging apparatus S, handlings are different from each other in the circumferential direction and the body axis direction in imaging, so that different dimensions in the x and y directions may be used. In addition, the number of the segments formed by the detector sub-pixels 11 with respect to the opening of the grid 9A may also be a value other than 3.

The size of the detector sub-pixel 11 is divided into four types according to the position in the detector pixel 10. That is, the detector sub-pixel 11 is divided into a detector sub-pixel 11A located below the grid 9A, a detector sub-pixel 11B not located below the grid 9A on one side in the x direction, a detector sub-pixel 11C located below the grid 9A in one side in the x direction and one side in the y direction, and a detector sub-pixel 11D located below the grid 9A on one side in the y direction.

By independently considering in the x direction and the y direction, the width of the detector sub-pixel 11 can be defined similar to the first embodiment.

That is, in a case where the pitch of the wall along the y direction of the grid 9A is $P_{gx}$, the wall thickness along the y direction of the grid 9 is $T_{gx}$, and the number of the segments of the detector sub-pixel 11 in the x direction with respect to the grid between the grids 9A is $N_x$, the width of the detector sub-pixels 11B and 11D in the x direction is set to as

[Math. 10]

$$\frac{(P_{gx} - T_{gx} - L_{split} \times 2)}{N_x}.$$

Herein, $L_{split}$ is in the range of 0 µm to 30 µm depending on detector system and energy. In addition, in a case where the pitch of the wall along the x direction of the grid 9A is $P_{gy}$, the wall thickness along the x direction of the grid 9 is $T_{gy}$, and the number of the segments of the detector sub-pixel 11 in the y direction with respect to the grid between the grids 9A is $N_y$, the width of the detector sub-pixels 11A and 11B in the y direction is set to as

[Math. 11]

$$\frac{(P_{gy} - T_{gy} - L_{split} \times 2)}{N_y}.$$

As a result, the sensitivity of the detector sub-pixel 11 can be brought closer to uniformity in consideration of the phenomenon that X-rays incident near the boundary L are detected across the two detector sub-pixels 11. As a result, the radiation imaging apparatus S can further improve the correction accuracy of the dead time under the high counting rate.

<<Modification Examples>>

The radiation imaging apparatus S according to the present embodiment is not limited to the configuration of the above embodiment, and various modifications are possible without departing from the gist of the invention.

Although the radiation imaging apparatus S according to the present embodiment has been described as an apparatus serving as the X-ray CT apparatus, it is not limited thereto, and may be applied to a transmission X-ray imaging apparatus, a positron emission tomography (PET) apparatus, a single photon emission computed tomography (SPECT) apparatus, a gamma camera, or the like.

In the present embodiment, the fact that the detector pixel 10 and the widths of the grids 9 and 9A correspond to each other is described, but the invention is not limited thereto. A configuration in which a plurality of detector pixels 10 are arranged between the widths of one grid or a configuration in which a plurality of grid holes correspond to one detector pixel 10 may be adopted.

In the one-dimensional grid in the first embodiment, the grid 9 has been described as being installed along the body axis direction (y direction), but the invention is not limited thereto. The grid 9 may be disposed along the circumferential direction (x direction) or may be disposed along the other direction.

REFERENCE SIGNS LIST

S X-ray CT apparatus (radiation imaging apparatus)
1 gantry
2 data processing device
3 image display device
4 bed
5 subject (object)
6 X-ray tube
7 detector panel
8 detector module
9 grid
10 detector pixel
11, 11A, 11B, 11C, 11D detector sub-pixel
12 readout circuit
13 semiconductor element
14 common electrode
15 individual electrode
$P_g$ pitch of grid
$T_g$ thickness of grid
$W_{11A}$, $W_{11B}$ width of detector sub-pixel
$G_A$, $G_B$ gap

The invention claimed is:

1. A radiation imaging apparatus comprising:
a grid that removes scattered beams that emanate from an object; and
a plurality of detector sub-pixels arranged so as to divide a gap between the grids into three or more segments,
wherein an area of each of detector sub-pixels located below wall surfaces of the grids is larger than that of each of the other detector sub-pixels in plan view.

2. The radiation imaging apparatus according to claim 1, wherein a size of each of detector sub-pixels not located below the wall surfaces of the grids is expressed as

[Math. 1]

$$\frac{(P_g - T_g - L_{split} \times 2)}{N}$$

(herein, $L_{split}$ is 0 μm to 30 μm), where $P_g$ represents a pitch between the grids, $T_g$ represents a thickness of each of the grids, and N represents the number of the segments formed by the detector sub-pixels between the grids.

3. The radiation imaging apparatus according to claim 2, wherein the grid is a one-dimensional grid.

4. The radiation imaging apparatus according to claim 2, wherein the grid is a two-dimensional grid.

5. A radiation imaging apparatus comprising:
a grid that removes scattered beams that emanate from an object;
a semiconductor element;
a common electrode formed on one surface of the semiconductor element; and
a divided electrode formed on the other surface of the semiconductor element,
wherein an area of each of the divided electrodes located below wall surfaces of the grids is larger than that of each of the other divided electrodes in plan view.

6. The radiation imaging apparatus according to claim 5, wherein a size of each of detector sub-pixels not located below the wall surfaces of the grids is expressed as

[Math. 2]

$$\frac{(P_g - T_g - L_{split} \times 2)}{N} - G$$

(herein, $L_{split}$ is 0 μm to 30 μm), where G represents a gap distance of the divided electrode, $P_g$ represents a pitch between the grids, $T_g$ represents a thickness of the grid, and N represents the number of the segments formed by the detector sub-pixels between the grids.

* * * * *